United States Patent [19]

Silvers

[11] 3,960,224
[45] June 1, 1976

[54] PRECISION CUT-OFF WEIGHING APPARATUS

[76] Inventor: Charles Silvers, 6500 N. Bay Road, Miami Beach, Fla. 33141

[22] Filed: June 6, 1975

[21] Appl. No.: 584,572

[52] U.S. Cl. .............................. 177/47; 128/214 E; 177/116; 177/DIG. 5; 200/85 R; 251/9
[51] Int. Cl.² ...................... A61B 5/14; G01G 13/30
[58] Field of Search ............... 177/47, 45, 116, 118, 177/60, DIG. 5; 128/214 E, 276, DIG. 6, DIG. 13; 200/85 R; 251/9, 7

[56] References Cited
UNITED STATES PATENTS

| | | | |
|---|---|---|---|
| 3,263,760 | 8/1966 | Waller | 177/116 X |
| 3,335,753 | 8/1967 | Kiser | 251/9 X |
| 3,557,789 | 1/1971 | Poitras | 177/118 X |
| 3,698,494 | 10/1972 | Gaudin | 177/118 |
| 3,778,808 | 12/1973 | Stevens | 177/45 X |

Primary Examiner—Joseph W. Hartary
Attorney, Agent, or Firm—Salvatore G. Militana

[57] ABSTRACT

A precision cut-off weighing apparatus having a balance type weighing device on which a desired weight is placed on one side and a bag to be filled with a fluid such as blood on the other. A magnet is mounted on the arm of the balance on which the bag is placed and a reed switch in a circuit mounted in proximity of the magnet to be influenced to close the circuit when the arm swings to the balanced position and bag has been filled to substantially the exact weight desired. The circuit is connected to a lever mounted on a support through which a tube extends to the bag whereby when the reed switch has been actuated, the lever swings to compress the tube and thereby prevent any further flow of fluid to the bag.

5 Claims, 6 Drawing Figures

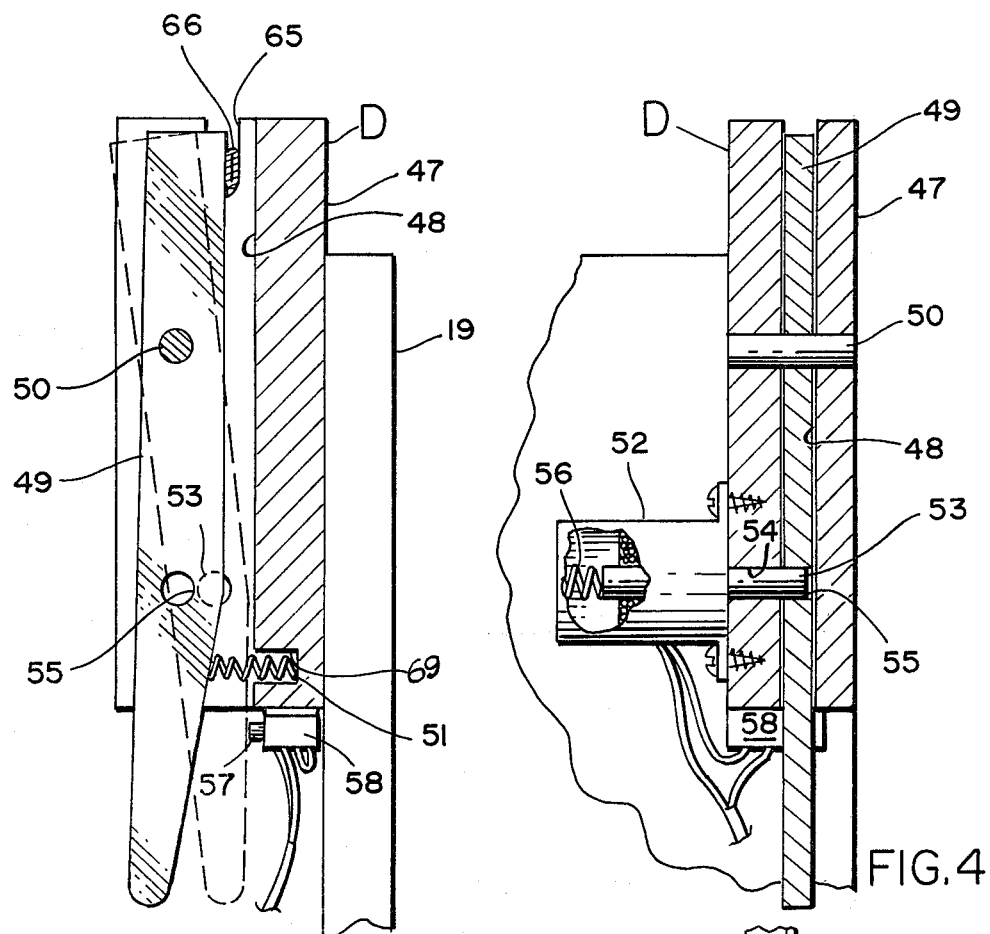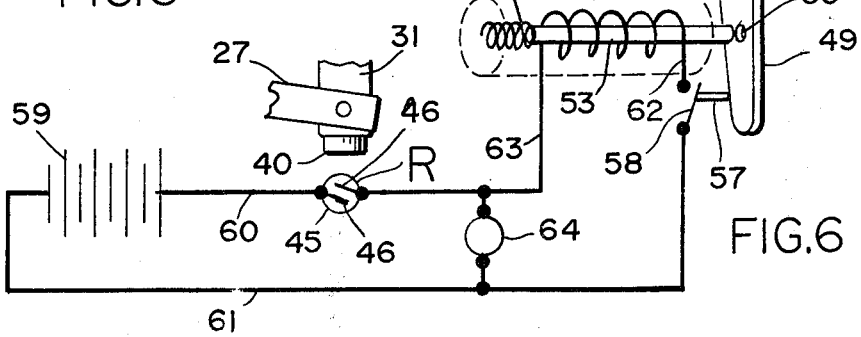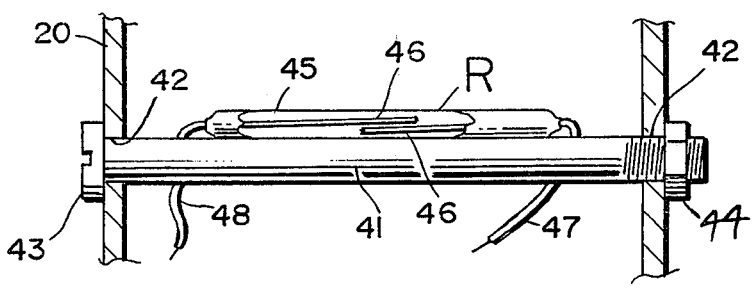

PRECISION CUT-OFF WEIGHING APPARATUS

BACKGROUND OF THE INVENTION

1. Field of the Invention

This invention relates to weighing devices and is more particularly directed to precision cut-off weighing apparatus combined with a weighing device.

2. Description of the Prior Art

With the advent of drawing blood from blood donors, Federal laws were passed limiting the amount of blood that can be drawn from individuals at any one time, and also the frequency of such blood donations. It became necessary to provide weighing devices that would cut-off the flow of blood as soon as the desired amount of blood was collected in a receptacle. However, these devices were either not accurate enough nor did they cut-off the flow of blood quickly and properly.

The present weighing device being used by most blood banks to assist in the collecting of a predetermined quantity of blood consists of a balance type scale on one side of which a weight is placed and on the other side a blood collecting bag is hung on a lever attached thereto. This type of device has been found not to be as accurate as required by the law. Also, if this scale is placed on a surface that is not level, a further error in weight will result. The present invention contemplates avoiding the above indicated objectsion of the present cut-off weighting devices.

SUMMARY OF THE INVENTION

Although the present invention is shown and described in connection with the drawing and collecting of blood from a blood donor, it may be used for collecting and packaging any fluid wherein an accurate weight or quantity is required. The Federal law limits the total amount of blood which can be drawn from a person, the amount being determined by the weight of the donor. To draw more than that permitted by law is a violation of the law and to draw less results in the loss of revenue to the blood bank.

For example, a person weighing less than 175 pounds may donate no more than 530 grams (500 millileters) of blood. At present, to be on the safe side, the operator will draw only 500 grams in order to be sure not to draw more than 530 grams. If the device being used collects only 500 grams of blood, then the blood bank will have only 500 grams available and als lose the profit on the 30 grams that could have been collected. The danger still exists with these devices that operate inaccurately, in that even when set to collect a smaller amount than the legal amount, the device will malfunction to draw and collect too much blood and thereby impair the health of the donor while at the same time violate the law.

Therefore, a principal object of the present invention is to provide a cut-off weighting apparatus that is positive and accurate in operation to collect in a bag a predetermined amount of fluid through a tube and to cut-off the flow of fluid to the bag at the precise moment by compressing or pinching off the tube.

Another object of the present invention is to provide a cut-off weighing device for collecting an accurate amount of fluid with a magnet mounted on one of the arms of a balance type scale and a reed switch in proximity to the magnet but out of the influence of its magnetism until a certain amount of fluid has been collected and the scale begins to swing passed the balanced position and the magnet moves sufficiently close to the reed switch to cause the magnetism to close the contacts of the reed switch and operate a device which cuts off the flow of fluid through the tube.

A further object of the present invention is to provide a precision cut-off weighing apparatus with a scale mounted on a wheeled cabinet and the cut-off mechanism mounted on a face board extending upwardly of the cabinet and the batteries and the like positioned within the cabinet to make the device portable and completely self-sufficient.

A still further object of the present invention is to provide a blood collecting apparatus that is accurate within the tolerances permitted by law of collecting blood from a donor which device is thereby most effective to collect the maximum amount of blood permitted and yet is very simple in operation.

With these and other objects in view, the invention will be best understood from a consideration of the following detailed description taken in connection with the accompanying drawings forming a part of this specification, with the understanding, however, that the invention is not confined to any strict conformity with the showing of the drawings but may be changed or modified so long as such changes or modifications mark no material departure from the salient features of the invention as expressed in the appended claims.

BRIEF DESCRIPTION OF THE DRAWINGS

In the drawings:

FIGS. 3 and 4 are cross sectional views taken along the lines 3—3 and 4—4 respectively of FIG. 1.

FIG. 5 is a cross sectional view taken along the line 5—5 of FIG. 2.

FIG. 6 is a schematic wiring diagram.

DESCRIPTION OF THE PREFERRED EMBODIMENT

Figure 1:
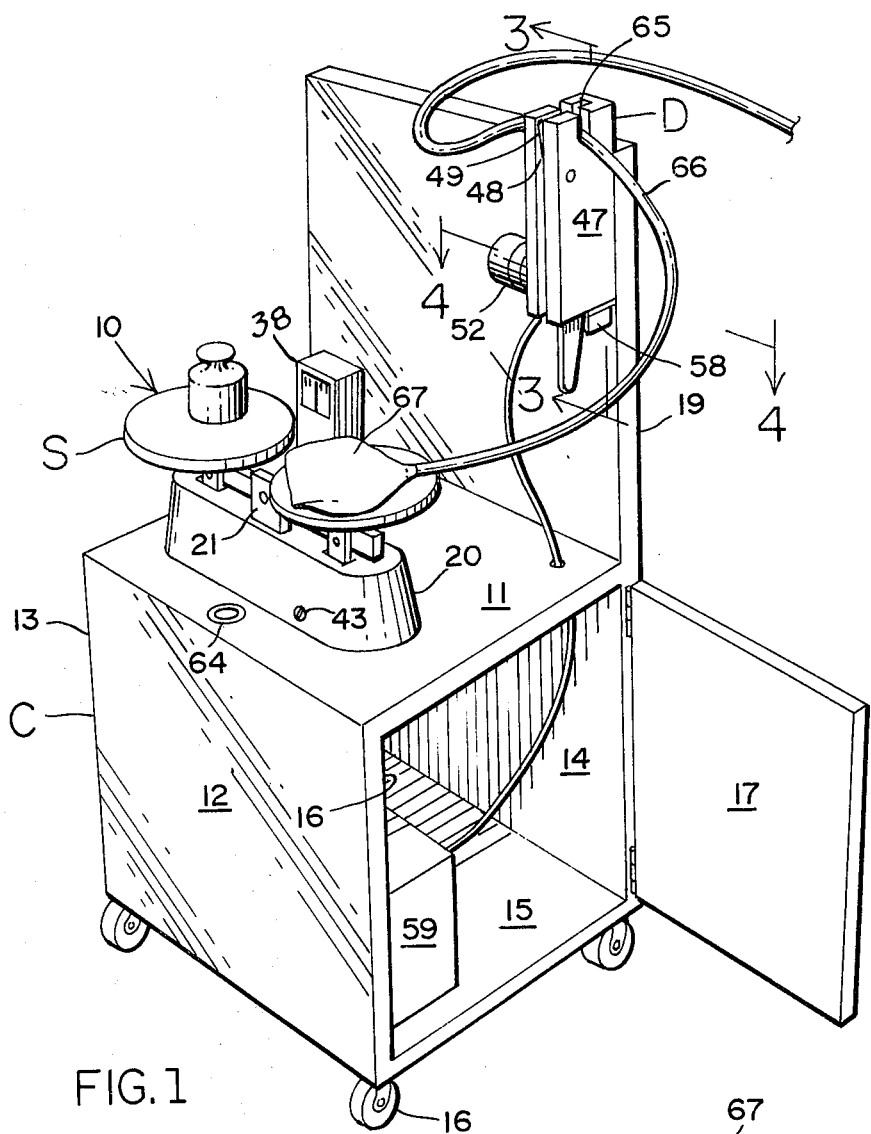
FIG. 1 is a perspective view of a precision cut-off weighing apparatus constructed in accordance with my invention.

Referring to the drawings wherein like numerals are used to designate similar parts throughout the several views, the numeral 10 refers to a precision cut-off weighing apparatus shown arranged in connection with a cabinet C for the sake of convenience of use and storage. The weighing apparatus 10 consists of a conventional balance scale S shown mounted on the top wall 11 of the cabinet C which consists of side walls 12, 13 and 14 extending upwardly of a bottom wall 15 to form a chamber 16 enclosed by a door 17 that is hinged along the edge of the side wall 14. The cabinet C is rendered mobile by casters 18 secured to the bottom wall 15.

The rear side wall 14 of the cabinet C extends upwardly above the top wall 11 as at 19 on which is mounted a liquid flow cut-off device D whose structure and function is explained in detail hereinafter. As stated above, the scale or balance S is conventional in construction consisting of a housing 20 at the mid-portion of which is an upwardly extending post 21. A balance lever 22 is pivoted as at 23 to the post 21 at the exact center of the lever 22. Within the chamber 24 formed in the housing 20 is a depending post 25 having a pivot pin 26 in exact vertical alignment with the pivot pin 23. Levers 27 and 28 which have their end pivotally mounted to the pivot pin 26 extend in opposite directions and are secured by pivot pins 29 and 30 to the lower ends of upright members 31 and 32. The balance arm or lever 22 is pivotally secured adjacent its end portions to the members 31 and 32 as at 33 and 34. Mounted on the top of the upright members 32 and 33 are circular plates 35 and 36 for receiving respectively threreon a weight and an article to be weighed. Secured to the balance lever 22 in vertical alignment with the pivot pin 23 is a pointer 37 that swings in unison with the balance lever 23. The pointer 37 is contained in a housing 38 mounted on the scale S. There is provided the usual markings 39 which indicate to the viewer when the pointer 37 is pointing at the balanced or unbalanced positions of the balance arm 22. Obviously when the scale S is in a balanced position, the pointer 37 will lie in coplanar relation with the large marking 39 while if there is an imbalance, the pointer 37 will be aligned to the right or left thereof.

The apparatus which has been incorporated with the above indicated conventional scale to form my precision cut-off weighing apparatus consists of a permanent magnet 40 secured to the lower end of the upright plate support 31. In proximity thereof, is a rod 41 which extends through openings 42 in the front and rear wall of the housing 20. The rod 41 is provided with a head portion 43 at one end for rotating the rod 42 while the other end is threaded for receiving a nut 44 to secure the rod 42 against inadvertant rotational movement so that when set at a predetermined position, the rod 42 will not rotate out of said position.

Cemented or otherwise secured on the rod 41 along its longitudinal axis is a glass receptacle 45 of a reed switch R. Within the receptacle 45 are two metallic reeds or terminals 46 that extend from the opposite ends of the sealed tube 45 and overlap in spaced relation with each other so that under normal circumstances the switch is in an open condition. However, as explained in detail hereinafter, when the reed switch R is influenced by the magnet 40, the magnetism will attract both reeds 46, to cause them to engage each other and thereby close a circuit in which the reed switch R is connected.

Mounted on the rear wall 19 is the fluid flow cutoff device D consisting of a rectangular support member 47 slotted along its full length as at 48 but only partially in depth as best shown by FIG. 3. Pivotally mounted in the slot 48 is a cut-off lever 49 pivoted about a pin 50 extending through the housing 47 and lever 49. The lower end of the lever 49 is yieldingly forced outwardly or in a cut-off position by a coil spring 51 mounted in a bore 69 formed in the housing 47 and engaging the inner edge of the cut-off lever 49 to compel the latter to swing in a clockwise direction as shown by FIG. 3. The lever 49 is normally locked in its extended or non cut-off position by a solenoid 52 mounted on the side wall of the housing 47 and having an armature 53 extending through bores 54 and 55 formed in the housing 47 and lever 49 respectively. The armature 53 is normally yieldingly forced outwardly by a coil spring 56 engaging the inner end of the armature 53. The bore 55 is so positioned that when the lever 49 is in its non cut-off position as shown by the dotted lines of FIG. 3, the armature 53 will be found extending in the bore 55 of the leveer 49. Also, with the lever 49 in this position, the latter will engage a plunger 57 of a cut-off switch 58 to close a circuit as explained hereinafter.

Mounted within the chamber 15 of the cabinet C is a battery 59 connected by a wire 60 to a terminal of the reed switch R whose other terminal is connected by a wire 61 to a terminal of the cut-off switch 58 whose other terminal is connected by a wire 62 to the solenoid 52. Wire 63 extends from the solenoid 52 to the reed switch R to complete the circuitry. Connected across the wires 61 and 63 is a light 64 which is mounted on the top wall 11 of the cabinet C to indicate when the apparatus is in use.

The housing 47 of the cut-off device 10 is further provided with a transversely disposed slot 65 which extends from the top edge thereof.

The slot 65 is sufficiently large to receive a tubing 66 which is positioned to be engaged and tightly compressed by the cut-off lever 49 when the latter swings to its solid line position. The tubing 66 extends from a person from whom the blood is being drawn to a plastic receptacle 67 which is placed on the plateform 35 of scale S. On the other platform 36 of the scale S is a weight which is to determine the exact amount of blood to be received by the receptacle 67 when the cut-off device D as explained hereinafter, will cut-off the flow of blood through the tube 66 so that the exact and desired amount will have been taken from the donor and deposited in the bag 67.

When it is desired to operate the cut-off device 10 for obtaining an accurate amount of blood from a donor, the exact weight 68 of blood desired to be obtained including the weight of the bags 67 and anticoagulate therein is placed on the platform 36 of the scale S and the bag or receptacle 67 is placed on the platform 35 with the tubing 66 extending approximately horizontally therefrom then up to the slot 65 wherein the tubing 66 is inserted. The free end of the tubing 66 is provided with a hypodermic needle (not shown) for drawing the blood from a donor thru the tubing 66 and collected in the receptacle 67. The lever 49 is pivoted to the position shown by dotted lines in FIG. 3 permitting the tubing to be received by the slot 65 and its lower end engaging the plunger 57 to close the switch 58. The solenoid 52 and light 64 cannot become activated since the circuit is still open at the reed switch R.

Figure 2:
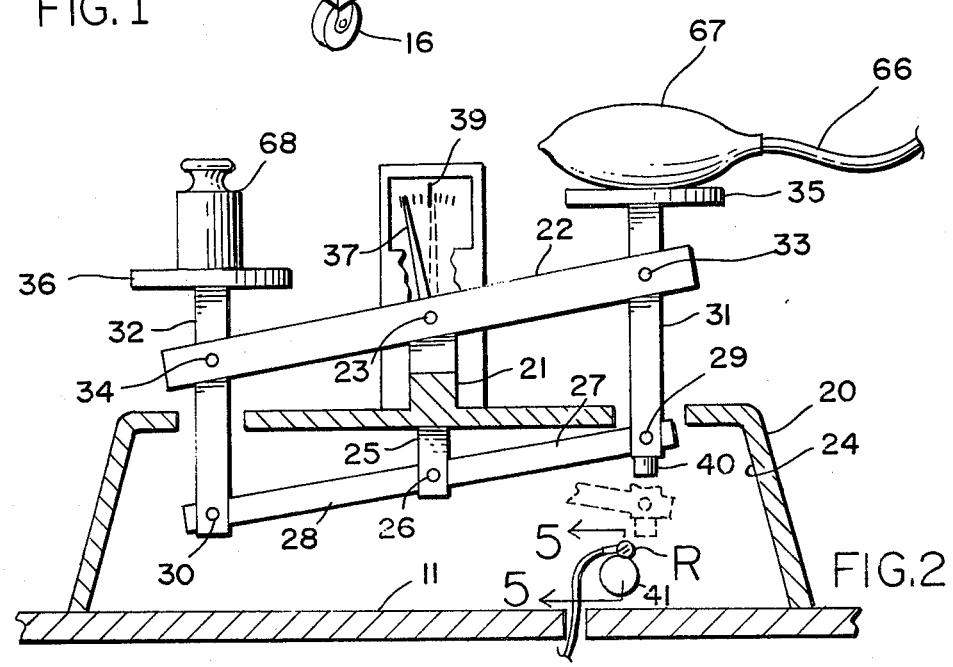
FIG. 2 is a fragmentary longitudinal cross sectional view of the weighing device.

The scale S is now in an unbalanced condition as indicated by FIG. 2 with the magnet 40 removed from influencing the reed switch R. As blood flows in the bag 67, the scale S will commence to tip in the direction of the movement of the indicator 37 toward the large mark 39. As the indicator 37 is arriving at the mark 39 to indicate that the desired amount of blood is about to be contained in the bag 67, the magnet 40 will be moving downwardly in the direction of the reed switch R. Immediately as the indicator 37 passes the mark 39, the magnet 40 finds itself at the distance from the reed switch R when the influence of the magnetism causes the metallic reeds 46 of the switch -R- to be attracted and thereby contact each other to close the circuit. As a result, the solenoid 52 becomes energized to cause the armature 53 to be retracted from the bore 55 against the spring forces 56 and thereby release the lever 49. The spring 51 now causes the lever 49 to pivot about its pivot 50 engage and compress the tubing 66 so that blood cannot flow therethrough. At the same time the light 64 is energized to notify the operator that the cut-off device 10 has completed the cycle of operation and the proper weight of blood is now contained in bag 67 and switch 58 opens to conserve battery power.

The tube 66 is now pinched off and cut by the operator close to the bag 67 which is removed from the scale S. The scale S now becomes unbalanced in favor of the weight side so that the other side rises carrying with it the magnet 40 away from the reed switch R out of the field of magnetism causing the reed 46 to move out of contact with each other and open the circuit. Now, to remove the tubing 66 from the slot 65 and replace it by another in order to repeat the cycle of operation, the operator pushes against the lower end of the lever 49, pivoting the upper end away from the slot 65 to release the tubing and permit another tubing to be received by the slot 65. At the same time, the switch 58 is closed and the armature 53 is forced by the spring 56 to slide into the bore 55 in the lever 49 with the spring 52 now exerting a force against the lever 49. The cut-off device 10 is now ready for the operator to place a tubing and bag on the device 10 as explained hereinabove to repeat the cycle of operation and for collecting another bag of blood having the exact quantity therein.

The position of the reed switch R with relation to the magnet 40 is very critical. For example, if the reed switch R is actuated by the magnet 40 before the proper amount of blood has been collected in the bag 67 then the reed switch R is too close to the magnet 40. This can be corrected by rotating the rod 41 by means of a screwdriver so that the reed switch R swings away from the magnet 40 to increase the distance between the magnet and the reed switch R. Now the scale must have added weight to bring the magnet 40 to the position wherein its magnetism will cause the reeds to close the circuit when the weight of bag 67 and its contents counterbalance the weight 68 at which time the proper amount of blood is contained in the bag.

What I claim as new and desire to secure by Letters Patent is:

1. A precision cut-off weighing apparatus comprising a balance having arm portions, means pivoting said arm portions for weighing articles placed thereon, a magnet mounted on one of said arms, reed switch means mounted in proximity of said magnet but out of the influence of the magnetic attraction of said magnet when said arm portions are in an unbalanced condition, a support, a lever pivotally mounted on said support, tubular member support means mounted on said support in the path of movement of said pivoted lever, restraining means mounted on said support preventing the pivotal movement of said lever, further means connected to said lever urging the pivotal movement of said lever, power operated means connected to said reed switch means and said restraining means whereby upon the swinging of said one arm portion in an unbalanced condition and said magnetic attraction causing said reed switch means to become closed, said restraining means is released and said further means effects the pivotal movement of said lever to swing in the direction of said tubular support means.

2. The structure as recited by claim 1 wherein said tubular member support means comprises a slotted portion formed on said support transversely to the path of movement of said lever.

3. The structure as recited by claim 2 wherein said restraining means comprises a solenoid having an armature, a bore in said lever in alignment with said armature and spring means urging the sliding movement of said armature into said bore.

4. The structure as recited by claim 3 wherein said further means comprises a spring mounted on said support engaging said lever and yieldingly urging the pivotal movement of said lever.

5. The structure as recited by claim 4 wherein said power operated means comprises light means operatively connected to said reed switch means and further switch means mounted on said support in proximity of said lever and connected to said solenoid whereby upon pivoting said lever in the direction away from said slotted portion said further switch means becomes energized to permit the energizing of said light means upon said reed switch means being actuated by said magnet.

* * * * *